(12) United States Patent
Yoshie

(10) Patent No.: US 8,597,178 B2
(45) Date of Patent: Dec. 3, 2013

(54) ACTIVE DRIVE TYPE MEDICAL APPARATUS AND DRIVE CONTROL METHOD

(75) Inventor: Michifumi Yoshie, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 644 days.

(21) Appl. No.: 12/535,234

(22) Filed: Aug. 4, 2009

(65) Prior Publication Data

US 2010/0030023 A1 Feb. 4, 2010

(30) Foreign Application Priority Data

Aug. 4, 2008 (JP) .................................. 2008-201219

(51) Int. Cl.
*A61B 1/00* (2006.01)

(52) U.S. Cl.
USPC .......................................... 600/146; 700/260

(58) Field of Classification Search
USPC ............................ 600/146, 139, 152; 700/260
See application file for complete search history.

(56) References Cited

U.S. PATENT DOCUMENTS

| | | | | |
|---|---|---|---|---|
| 5,354,162 | A | * | 10/1994 | Burdea et al. ........................ 414/5 |
| 5,759,151 | A | * | 6/1998 | Sturges ............................ 600/146 |
| 5,807,376 | A | * | 9/1998 | Viola et al. ......................... 606/1 |
| 5,813,813 | A | * | 9/1998 | Daum et al. ....................... 414/7 |
| 6,301,526 | B1 | * | 10/2001 | Kim et al. ...................... 700/260 |
| 6,569,084 | B1 | | 5/2003 | Mizuno et al. |
| 2004/0034279 | A1 | | 2/2004 | Arai et al. |
| 2005/0075538 | A1 | * | 4/2005 | Banik et al. .................... 600/146 |
| 2005/0119527 | A1 | | 6/2005 | Banik et al. |
| 2006/0069310 | A1 | | 3/2006 | Couvillon, Jr. |
| 2008/0262538 | A1 | * | 10/2008 | Danitz et al. ................... 606/205 |
| 2010/0016990 | A1 | * | 1/2010 | Kurtz ............................... 623/24 |
| 2011/0065994 | A1 | * | 3/2011 | Kudoh et al. ................. 600/146 |
| 2012/0179068 | A1 | * | 7/2012 | Leo et al. ....................... 600/587 |

FOREIGN PATENT DOCUMENTS

| | | |
|---|---|---|
| EP | 1 908 389 A1 | 4/2008 |
| JP | 08-118275 | 5/1996 |
| JP | 08-174458 | 7/1996 |
| JP | 2000-279376 | 10/2000 |
| JP | 2003-071760 | 3/2003 |

(Continued)

OTHER PUBLICATIONS machine translation of JP2000-279376 Oct. 2000.*

(Continued)

*Primary Examiner* — Christopher Mahoney
(74) *Attorney, Agent, or Firm* — Scully, Scott, Murphy & Presser, P.C.

(57) ABSTRACT

An active drive type medical apparatus includes: an active mechanism having a rotatable joint provided near the distal end of a long member; an active mechanism driving section; a position/attitude detecting section configured to detect a position/attitude of the active mechanism; an instruction input section for performing instruction input of the position/attitude of the active mechanism; and a force calculating section configured to calculate, on the basis of the instruction input of the position/attitude, a force corresponding to a net external force acting on the active mechanism, by subtracting an estimated driving force estimated in the case where the active mechanism in a no-load state is driven, from a driving force required in the case where the active mechanism is actually driven by the active mechanism driving section from the position/attitude before the instruction input to the instructed and inputted position/attitude.

15 Claims, 9 Drawing Sheets

(56) References Cited

FOREIGN PATENT DOCUMENTS

| | | |
|---|---|---|
| JP | 2003-245246 | 9/2003 |
| JP | 2007-185355 | 7/2007 |
| JP | 2007-283115 | 11/2007 |
| WO | WO 2004/086957 A2 | 10/2004 |

OTHER PUBLICATIONS

Extended European Search Report dated Nov. 5, 2009.
Japanese Official Action dated Dec. 25, 2012 from related application JP 2008-201219 together with a partial English language translation.

* cited by examiner

ACTIVE DRIVE TYPE MEDICAL APPARATUS AND DRIVE CONTROL METHOD

CROSS REFERENCE TO RELATED APPLICATION

This application claims benefit of Japanese Application No. 2008-201219 filed in Japan on Aug. 4, 2008, the contents of which are incorporated herein by this reference.

BACKGROUND OF THE INVENTION

1. Field of the Invention

The present invention relates to an active drive type medical apparatus and a drive control method, in which an active mechanism is driven on the basis of an instruction input from an instruction input section.

2. Description of the Related Art

In recent years, an endoscope has been widely used in a medical field and an industrial field. In the medical field, a treatment instrument is also widely used in combination with an endoscope.

As the endoscope serving as such medical apparatus, there are practically used a type in which a bending section provided at the distal end side of an insertion section is bent by a manual operation, and a type in which the operability is improved by providing an electrical bending active mechanism that is configured to be electrically driven by using a motor so as to bend the bending section.

Also, as the treatment instrument, there is used a type including an active mechanism configured to electrically drive, on the basis of an operation on the operator's side, a treatment section as the active mechanism in which a rotatable joint is provided on the distal end side, and the like, of the treatment instrument.

For example, an electric bending endoscope is disclosed in Japanese Patent Application Laid-Open Publication No. 2007-185355.

In the electric bending endoscope as the preceding example, a control section rotationally drives a motor as a bending driving section via a motor driver on the basis of an instruction input performed by an operator from an instruction input section (or instruction operation section), and the rotating motor pulls a bending wire so as to thereby drive and bend a bending section provided in an insertion section.

Further, the preceding example is configured such that data of tension, as force sense information, which acts on the bending section via, for example, the bending wire serving as a bending state detecting section for detecting the bending state of the bending section, is fed back by being superposed on the value of the instruction input by a joystick serving as the instruction input section, so as to thereby enable the operator to sense the state of the insertion section as the force sense information. Further, the tension data is set so as to generate a reaction force against the instruction by the joystick.

In the case of a medical apparatus (or an active drive type medical apparatus), such as an endoscope and a treatment instrument, which is used by inserting a long member, such as an insertion section, into a body cavity, it may be desired to detect that the active mechanism on the distal end side of the long member is brought into contact with a body wall, and the like.

However, in the case of a thin insertion section and a thin treatment instrument, it is difficult to mount a force sensor at the distal end of the insertion section, and the like. For this reason, there is adopted a configuration in which a tension sensor is provided on the operator's side similarly to the above described preceding example, and in which the driving force to operate the active mechanism is measured by the tension sensor so that the measured driving force is fed back.

SUMMARY OF THE INVENTION

An active drive type medical apparatus according to the present invention, which has a rotatable joint provided near the distal end of a long member, includes:

an active mechanism whose position and/or attitude is changed according to the rotation of the joint;

an active mechanism driving section configured to electrically drive the active mechanism;

a position/attitude detecting section provided near the rear end of the long member, and configured to detect the position and/or attitude of the active mechanism;

an instruction input section used to perform instruction input of the position and/or attitude of the active mechanism; and a force calculating section configured to calculate, on the basis of the instruction input of the position and/or attitude from the instruction input section, a force corresponding to a net external force acting on the active mechanism by subtracting an estimated driving force, which is estimated in the case where the active mechanism in a no-load state is driven by the active mechanism driving section from the position and/or attitude of the active mechanism before the instruction input to the position and/or attitude instructed and inputted from the instruction input section, from a driving force, which is required in the case where the active mechanism is actually driven by the active mechanism driving section from the position and/or attitude of the active mechanism before the instruction input to the position and/or attitude instructed and inputted from the instruction input section.

A drive control method according to the present invention includes:

an instruction input step of operating an instruction input section and performing, to an active mechanism which includes a rotatable joint provided near the distal end of a long member and the position or attitude of which is changed according to the rotation of the joint, instruction and input to change a present position/attitude to a target position/attitude;

a driving step of driving the active mechanism from the present position/attitude to the target position/attitude;

a calculation step of calculating an external force acting on the active mechanism by subtracting an estimated driving force required to drive the active mechanism in a no-load state from the present position/attitude to the target position/attitude from a driving force required to actually drive the active mechanism from the present position/attitude to the target position/attitude; and an application step of applying the calculated external force to the instruction input section.

DETAILED DESCRIPTION OF THE PREFERRED EMBODIMENTS

In the following, embodiments according to the present invention will be described with reference to the accompanying drawings.

Embodiment 1

Figure 1:
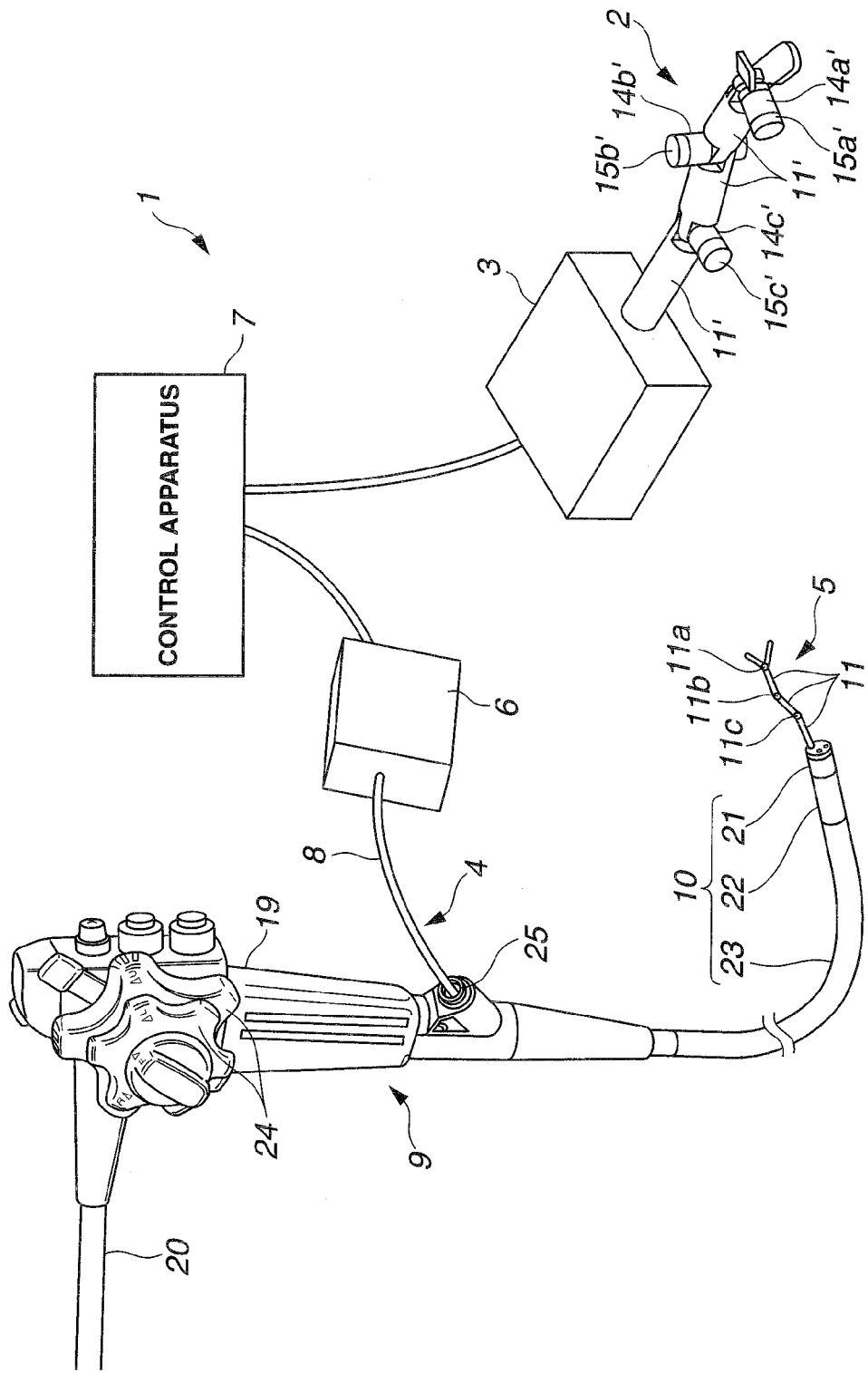
FIG. 1 is a perspective view showing an appearance of a treatment instrument system of embodiment 1 according to the present invention.

As shown in FIG. 1, a treatment instrument system 1 of embodiment 1 according to the present invention is configured by a treatment instrument which has an active function to be used together with, for example, an endoscope 9.

The treatment instrument system 1 includes a master section 2 as an instruction input section which performs instruction input, a master driving section 3 which drives the master section 2, a treatment instrument main body 4 which performs treatment, a slave driving section 6 (as an active mechanism driving section) which drives an active mechanism 5 as a slave configuring a treatment section provided at the distal end of the treatment instrument main body 4, and a control apparatus 7 which controls both the driving sections 3 and 6.

The treatment instrument main body 4 has a long member 8 and the active mechanism 5 provided at the distal end of the long member 8. The long member 8 and the active mechanism 5 are inserted into a treatment instrument channel of the endoscope 9.

The endoscope 9 has an insertion section 10 as a long member inserted into a body cavity, an operation section 19 provided at the rear end of the insertion section 10, and a universal cable 20 which extends from the operation section 19. The end section of the universal cable 20 is connected to a light source apparatus and a signal processing apparatus (both not shown).

Further, the insertion section 10 has a distal end section 21 provided at the distal end thereof, a bending section 22 which is provided at the rear end of the distal end section 21 and which is freely bendable, and a long flexible section 23 which extends from the rear end of the bending section 22 to the front end of the operation section 19.

Further, the bending section 22 is bent in an arbitrary direction including upper, lower, left and right, by an operator rotating a bending knob 24 provided at the operation section 19.

Further, a treatment instrument insertion port 25 is provided near the front end of the operation section 19. The treatment instrument insertion port 25 communicates with the treatment instrument channel provided in the longitudinal direction of the insertion section 10. The treatment instrument channel is opened at the distal end section 21.

Thus, when, as shown in FIG. 1, the treatment instrument main body 4 is inserted into the treatment instrument insertion port 25 from the distal end side of the treatment instrument main body 4 (by using, as a guide member for guiding the insertion of the treatment instrument main body 4, the insertion section 10 in which the treatment instrument channel is provided), the distal end side of the treatment instrument main body 4 is made to project from the opening at the distal end of the treatment instrument channel so that medical treatment can be performed to a lesion area (not shown), and the like.

Further, in the present embodiment, in order to improve the operability by the operator, the instruction input section, with which the operator performs instruction and input, is formed by the master section 2 having a shape and structure which simulate (or are similar to) the active mechanism 5.

The active mechanism 5, which forms the treatment section, has a plurality of rotatable joints as movable sections. Specifically, the active mechanism 5 includes distal end cup pieces and joint pieces (or bending pieces) 11, 11 and 11 which are rotatably connected by joint shafts (rotary shafts) 11a, 11b and 11c. For example, the distal end cup pieces, the proximal ends of which are rotatably connected to the joint piece 11 adjacent to the distal end cup pieces by the joint shaft 11a, are opened and closed around the joint shaft 11a. Note that here, for simplification, it is assumed that a pair of the distal end cup pieces are opened and closed around the joint shaft 11a in linkage with each other, or that one of the pair of distal end cup pieces is opened and closed around the joint shaft 11a.

The master section 2 is formed so as to have a shape and structure which simulate the active mechanism 5. However, the active mechanism 5 is formed to be thin so as to be able to be inserted into the treatment instrument channel, while the master section 2 is formed to have a size larger than that of the active mechanism 5 so as to be able to be easily operated by hand (finger) by the operator.

The master section 2 includes distal end cup pieces and joint pieces 11', 11' and 11' which are rotatably connected by the joint shafts 11a', 11b' and 11c'. For example, the distal end cup pieces, the proximal ends of which are rotatably connected to the joint piece 11' by the joint shaft 11a', are opened and closed around the joint shaft 11a'. As described above, it is assumed that a pair of the distal end cup pieces are opened and closed around the joint shaft 11a' in linkage with each other, or that one of the pair of distal end cup pieces is opened and closed around the joint shaft 11a'.

When the operator grasps the master section 2 located on the operation input section side so as to perform an operation for instruction input, specifically when the operator performs an operation to respectively rotate the distal end cup pieces and the joint pieces 11', 11' and 11' around the joint shafts 11a', 11b' and 11c' so as to change the positions of the respective sections and/or the attitude (based on the plurality of positions), the states of the positions and/or the attitude are detected. Thereby, the control apparatus 7 controls the driving sections 3 and 6 so that the active mechanism 5 located on the treatment section side is also rotationally driven (to be bent) around the joint shafts 11a, 11b and 11c so as to also assume the corresponding positions and/or attitude.

That is, when the operator grasps the master section 2 and performs an operation to set the active mechanism 5 to a position and/or attitude state at which the operator desires to perform treatment, the operation is detected by position and/or attitude detecting means. Then, the control apparatus 7 drives the active mechanism 5 to follow the position and/or attitude of the master section 2 and thereby sets the active mechanism 5 to the same position and/or attitude state.

Figure 2:
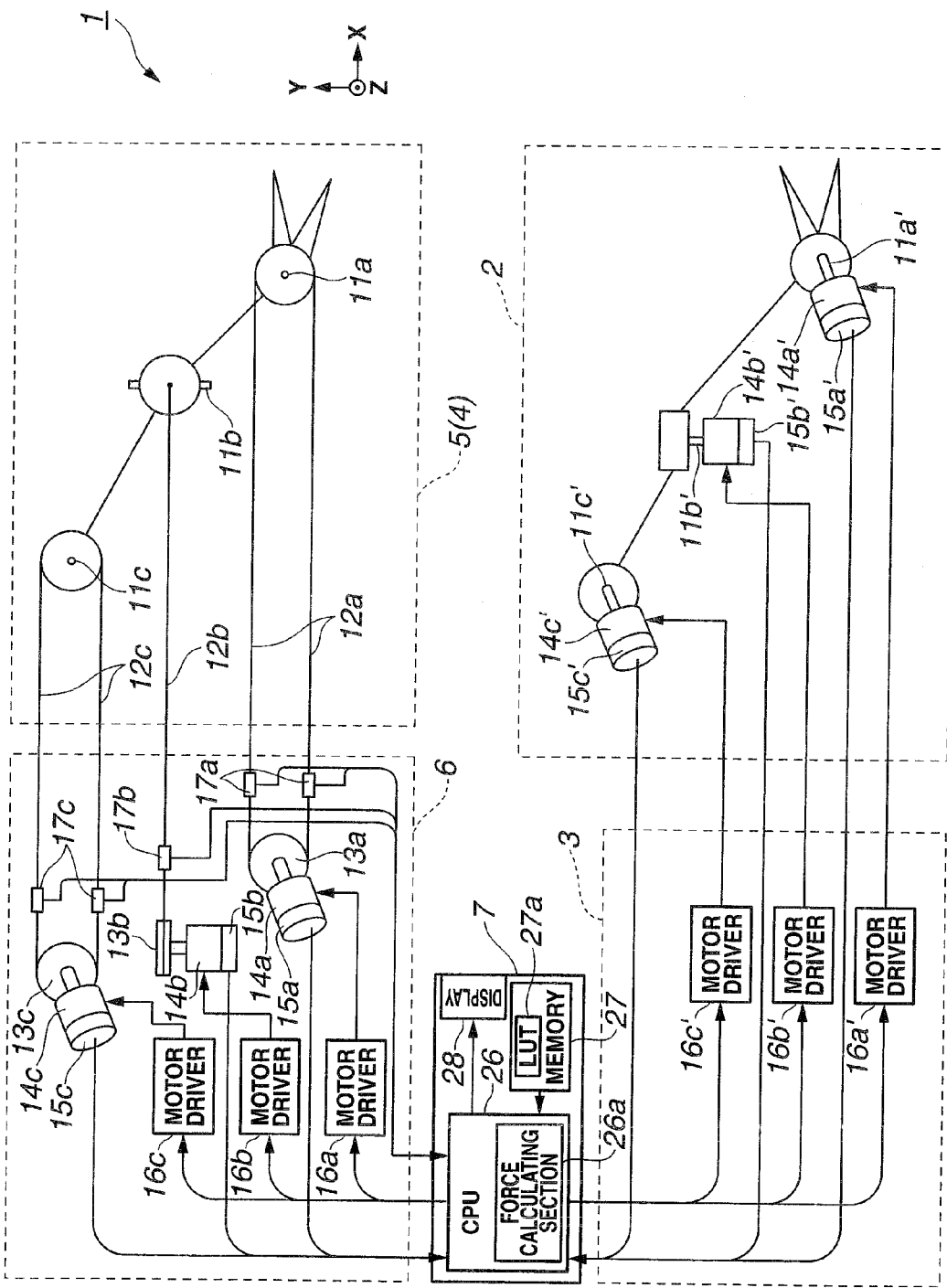
FIG. 2 is a figure showing a configuration of the treatment instrument system of embodiment 1.

FIG. 2 shows a schematic configuration of the treatment instrument system 1. Note that FIG. 2 schematically illustrates the joint shafts 11a to 11c and 11a' to 11c'.

As described above, the plurality of joint shafts 11a to 11c, and the plurality of joint shafts 11a' to 11c' are respectively provided in the active mechanism 5 and the master section 2.

Specifically, when the paper surface is set as the X-Y plane as shown in FIG. 2, the joint shaft 11a at the most distal end of the active mechanism 5 is set in the Z-axis direction vertical to the paper surface, and the next joint shaft 11b is set in the Y-axis direction in the paper surface. Also, the next joint shaft 11c is set in the Z-axis direction vertical to the paper surface.

The joint shafts 11a' to 11c' on the side of the master section 2 are also configured similarly to the joint shafts 11a to 11c.

Further, wires 12a, 12a; 12b, 12b; 12c, 12c which transmit the rotational force around the respective joint shafts 11a to 11c are inserted in (the joint pieces 11 of) the active mechanism 5.

The distal ends of the wires 12i, 12i (i=a to c) are respectively fixed to the distal end cup pieces or the joint pieces 11 around the joint shafts 11i, while the rear ends of the wires 12i, 12i are respectively hooked and fixed to pulleys 13i in the slave driving section 6.

Further, the pulleys 13i are respectively attached via gears (not shown) to the rotary shafts of motors 14i serving as driving sections. There are respectively attached to the rotary shafts of the motors 14i, for example, rotary encoders (hereinafter abbreviated simply as encoders) 15i, each of which serves as an angle sensor, or a position sensor, for detecting the angle of rotation (rotation angle) of the rotary shaft.

Note that the attitude of the active mechanism 5 is detected by the plurality of position sensors. Therefore, the encoders 15a to 15c form position and/or attitude detecting sections which detect the positions and/or attitude. The motors 14i configuring the driving sections are rotationally driven by receiving motor drive signals from motor drivers 16i, respectively.

Further, tension sensors 17i, 17i for detecting the force (specifically tension) acting on the respective wires 12i, 12i are attached to, for example, the rear end side of the wires 12i, 12i. Note that the sensors are not limited to the tension sensors 17i, and torque sensors, or the like, for detecting the torque of the motors 14i may also be used.

The detection signals of the tension sensors 17i and the detection signals of the encoders 15i are inputted into a CPU 26 which configures the control apparatus 7. The CPU 26 controls the rotation of the motors 14i via the motor drivers 16i.

Further, the configuration of the master section 2 is the same as that of the active mechanism 5, and hence the components of the master section 2 are indicated by attaching an apostrophe to the reference characters indicating the components of the active mechanism 5. However, the joint shafts 11i' are respectively rotationally driven in the state of being connected to (geared) motors 14i' (without via the wires 12i in the case of the active mechanism 5). For this reason, there is shown in FIG. 2 the state where the motors 14i' and encoders 15i', which configure a part of the master driving section 3, are provided on the side of the master section 2 similarly to the case of FIG. 1.

When the master section 2 and the master driving section 3 are represented so as to be divided at the positions of the joint shafts 11i', (that is, are represented in correspondence with the manner of dividing the active mechanism 5 and the slave driving section 6 in FIG. 2), the configuration of the master driving section 3 is the same as that of the slave driving section 6 except that the tension sensors 17i in the slave driving section 6 are not provided. Thus, the components in the master driving section 3 are indicated by attaching an apostrophe to the reference characters indicating the components in the slave driving section 6.

The signals which are detected by encoders 15a' to 15c' and which correspond to the instruction input operation by the operator with the master section 2 are inputted as position and/or attitude information into the CPU 26 which configures the control apparatus 7.

That is, the direction of rotation and the angle of rotation (hereinafter defined as rotation angle) of the joint shafts 11a' to 11c' which configure the master section 2 operated by the operator, are detected by the encoders 15a' to 15c', and the encoder output signals are inputted as detection signals into the CPU 26. At that time, the CPU 26 compares the detection signals from the encoders 15a' to 15c' with detection signals from the encoders 15a to 15c for detecting the rotation angle of the joint shafts 11a to 11c on the side of the active mechanism 5 (that is, which configure the active mechanism).

Then, the CPU 26 generates detection signals of difference values obtained by subtracting the detection signals of the encoders 15a to 15c from the detection signals from the encoders 15a' to 15c', and sets the difference values as command values for driving the active mechanism 5, so as to rotate the distal end cup pieces or the joint pieces 11 around the joint shafts 11a to 11c via the motor drivers 16a to 16c.

Thereby, the position and/or attitude of the active mechanism 5 before the instruction input is controlled so as to follow the position and/or attitude instructed and inputted by the master section 2. Note that the position and/or attitude before the instruction input is also referred to as the present position and/or attitude.

Further, in the present embodiment, the forces acting to rotate the distal end cup pieces and the joint pieces 11 around the joint shafts 11a to 11c are detected by the tension sensors 17a to 17c, and the detection signals are also inputted into the CPU 26 as force sense information (or force information).

In this case, the CPU 26 has a function of a force calculating section 26a which calculates net external forces actually acting on the distal end cup pieces and the joint pieces 11 of the active mechanism 5 on the basis of estimation from the detection signals measured by the tension sensors 17i (i=a to c). Note that motor torque sensors which measure the motor torque of the motors 14i may also be used instead of the tension sensors 17i. Note that in the case where gears are respectively connected to the motors 14i, the motors may be handled as geared motors. Also, in the case where the motors 14i are motors without the gears, the motors can be similarly handled.

The CPU 26 calculates as follows the external forces from the detection signals of the tension sensors 17i, and the like, by the function of the force calculating section 26a.

In this case, the CPU 26 acquires the driving force, which is used to actually drive the active mechanism 5, from the detection signals of the tension sensors 17i, and calculates the force corresponding to the external force by subtracting, from the acquired driving force, the driving force (referred to as estimated driving force) which is estimated beforehand in a no-load state without the action of the external force. Further, in this case, the CPU 26 stores beforehand the information for calculating the estimated driving force in a memory 27 as an information storage section.

The tension sensors 17i, and the like, actually detect (measure) the force Fm generated by the (geared) motors 14i. In the case where the force for moving the motor $14i$ itself is set as Fpm, where the force for moving the distal end cup piece and the joint piece 11 of the active mechanism 5 in the state of no external force (that is, in a no-load state) is set as Fs, and where the force corresponding to the net external force acting on the distal end cup piece or the joint piece 11 of the active mechanism 5 is set as Fo, the force Fm generated by the motor $14i$ becomes the sum of these forces. That is, the following equation is obtained.

$$Fm = Fpm + Fs + Fo \qquad (1)$$

The (force calculating section 26a of) CPU 26 acquires the force Fm generated by the motor $14i$, as described above, by the tension sensor $17i$, and the like.

Further, the operator, such as a surgeon, desires to sense the force Fo corresponding to the net external force, and hence the equation (1) is deformed as follows.

$$Fo = Fm - (Fpm + Fs) \qquad (2)$$

The (force calculating section 26a of) CPU 26 calculates the force Fo corresponding to the net external force in the equation (2).

That is, the CPU 26 calculates the force Fo corresponding to the net external force, which the operator desires to sense, by subtracting the force (Fpm+Fs) which is the estimated driving force in the state of no external force (that is, in a no-load state without the action of the external force), from the force Fm which is the driving force required to actually drive the side of the active mechanism 5. In the following, this external force is described as Fo.

Further, the force Fpm for driving the motor $14i$ itself is expressed as follows by using the viscous friction force Fpmn acting on the motor $14i$ itself and the inertia force Fpmi of the motor $14i$.

$$Fpm = Fpmn + Fpmi \qquad (3)$$

Here, there will be described the viscous friction force Fpmn in the equation (3). When a fixed voltage is applied to the (geared) motor $14i$ in a no-load state, the motor $14i$ is driven at a constant speed.

Figure 3:
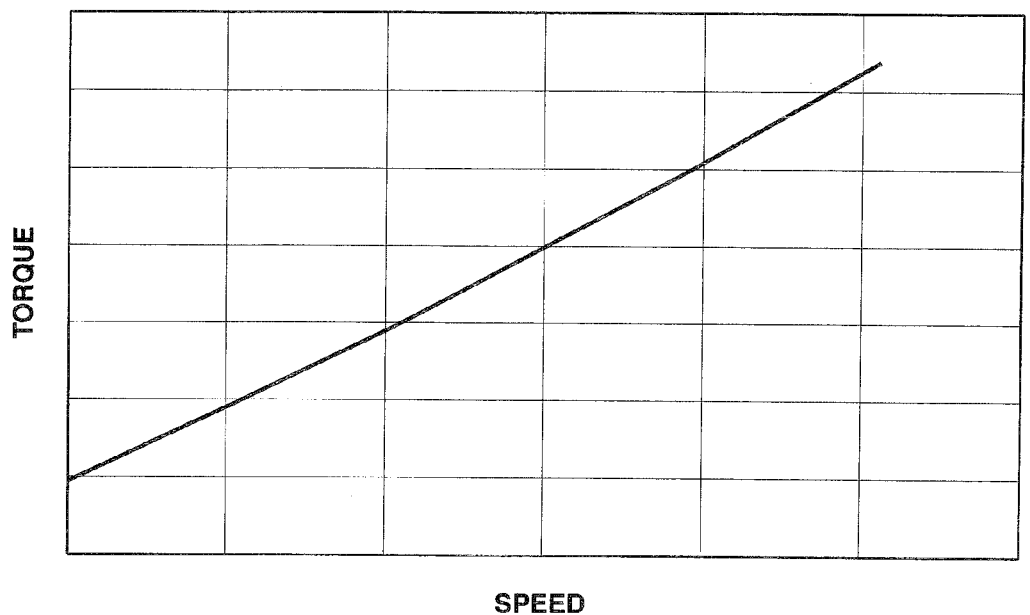
FIG. 3 is a characteristic diagram showing a relationship between the torque and the speed.

The speed-torque curve as shown in FIG. 3 is obtained by measuring the torque of the motor $14i$ while changing the voltage applied to the motor $14i$.

In the case of actual control, the information on an approximate equation of the graph is stored beforehand, for example, in the memory 27 shown in FIG. 2, which can be referred to by the CPU 26. The CPU 26 can acquire the value of viscous friction force Fpmn of the (geared) motor $14i$ by calculating the torque corresponding to the speed in the state controlled by the CPU 26. Note that the memory 27 may be configured so as to be provided in the CPU 26.

Next, there will be described the inertia force Fpmi of the motor $14i$. The rotor inertia of the motor $14i$ is set as JM, and the rotor inertia of the gear is set as JG. When the angular acceleration of the motor $14i$ is set as $\alpha$, the inertia force Fpmi can be obtained as follows.

$$Fpmi = JM \times \alpha + JG \times \alpha = (JM + JG) \times \alpha \qquad (4)$$

Next, there will be described the force Fs on the right side of the equation (2), for driving the joint piece 11 of the active mechanism 5.

The force Fs depends on the mechanical structure of the active mechanism 5, and may often have a large individual difference.

Thus, it is possible to acquire information which relates the rotation angle to the torque by methods, such as by beforehand measuring and obtaining the torque (force) required to set the joint piece 11 at each rotation angle within the range of rotation angle at which the joint piece 11 can be rotated in a no-load state.

The information acquired by the measurement, and the like, in this way is formed into, for example, a table as information which relates the rotation angle to the torque, so as to be stored in, for example, the memory 27. When actually performing the rotation control, the CPU 26 can acquire, by referring to the table, the torque value corresponding to the rotation angle to be set or the set rotation angle. The torque value is the value of the force Fs for driving the distal end cup piece or the joint piece 11 of the active mechanism 5.

Further, when the joint shafts $11i$ of the active mechanism 5 are rotated to bend by the pulling of the wires $12i$, the torque values required to make the distal end cup pieces or the respective joint pieces 11 rotate around the joint shafts $11a$ to $11c$ are changed in dependence upon the state of the curved paths of the wires $12i$.

Therefore, in the case where the active mechanism 5 has, for example, three joint shafts $11a$ to $11c$, and where the rotation is performed around the respective joint shafts, the torque values (rotations) are influenced by each other. Therefore, it is preferred to create, for example, tables by measuring three torque values for each of all the rotation angles which can be taken around the respective joint shafts. In this way, there are completed, for example, by the measurement, tables which relate the rotation angles $\theta 1$, $\theta 2$ and $\theta 3$ around the respective joint shafts to the torque values Tu1, Tu2 and Tu3 required for the rotation around the respective joint shafts.

Thus, it is possible to more accurately calculate or estimate the force Fs by storing the tables in, for example, the memory 27. It is possible to more accurately calculate or estimate the force Fo from the equation (2) by using the force Fs. Note that in FIG. 2, it is shown that the tables are stored in the memory 27 as a look-up table (hereinafter abbreviated as LUT) 27a.

Note that in the case where the treatment instrument main body 4 is inserted into the treatment instrument channel of the endoscope 9 so as to be used, the value of the force Fs for moving the joint pieces 11 of the active mechanism 5 around the joint shafts changes depending on the curved state of the treatment instrument channel of the endoscope 9, that is, including the curved state of the insertion section 10.

For this reason, it may also be configured such that the value of the force Fs is calculated by utilizing the information on the attitude, such as the curving of the insertion section 10 of the endoscope 9, as will be described below (described below in embodiment 3).

When the (force calculating section 26a of) CPU 26 calculates the external force Fo, then the CPU 26 sends the information of the external force Fo to a display section 28 (as a presentation section of force information), which is provided in the front panel, and the like, of the control apparatus 7 shown in FIG. 2, and displays the value of the external force Fo in the display section 28, so as to present or notify the information of the external force Fo to the operator, and the like.

Further, in order to effect the rotation around joint shafts $11i'$ of the master section 2 in correspondence with the external force Fo, the CPU 26 respectively provides motor drivers $16i'$ with, for example, current instruction values corresponding to the external force Fo, so as to rotate the motors $14i'$. The forces corresponding to the external force Fo are outputted by the rotation of the motors $14i'$ to the joint pieces $11i'$ of the master section 2, which correspond to the joint pieces $11i$ of the active mechanism 5.

Then, the operator can sense the magnitude and direction of the external force Fo by the hand (finger) operating the master section 2, on the basis of the forces fed back to act on (drive) the distal end cup pieces or the joint pieces 11i', which correspond to the distal end cup pieces or the joint pieces 11i of the active mechanism 5.

Figure 4A:
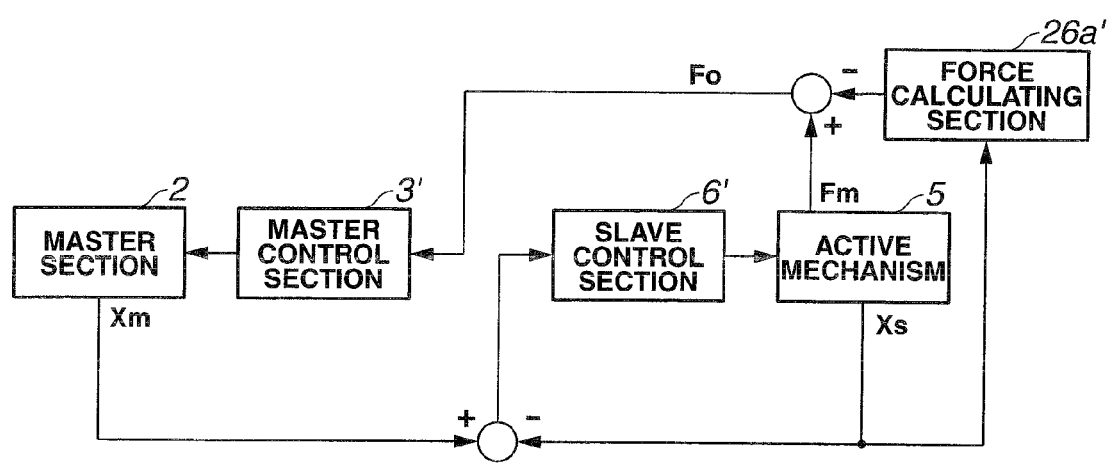
FIG. 4A is a block diagram showing a configuration of a control system of embodiment 1.

An example of a control system of the control apparatus 7 in this case is configured as shown in a block diagram in FIG. 4A.

In the control system shown in FIG. 4A, the position information Xm of the position generated by the input instruction inputted into the master section 2 serving as the instruction input section is subtracted from the position information Xs of the active mechanism 5 as the treatment section, and the subtracted position information is sent to a slave control section 6'. The slave control section 6' performs position control (position drive) of the active mechanism 5 on the basis of subtracted position information (Xm–Xs). The position information Xs is sent to a force calculating section 26a'.

The force information of the force calculating section 26a' is subtracted from the force information of the force Fm which actually acts on the active mechanism 5, and the force information corresponding to the external force Fo is sent to a master control section 3'. The master control section 3' performs the force control of the master section 2 on the basis of the force information corresponding to the external force Fo.

Note that in FIG. 4A, the master control section 3' corresponds to a configuration including, in addition to the function of the master driving section 3, a control section in the control apparatus 7, which section controls the master driving section 3. Further, the slave control section 6' is represented by a configuration including, in addition to the function of the slave driving section 6, a control section in the control apparatus 7, which section controls the slave driving section 6. Further, the force calculating section 26a' corresponds to a calculating section which calculates the force information (the estimated driving force (Fpm+Fs) in the equation (2)) before the external force Fo is calculated by the subtraction in the above described force calculating section 26a.

Figure 4B:
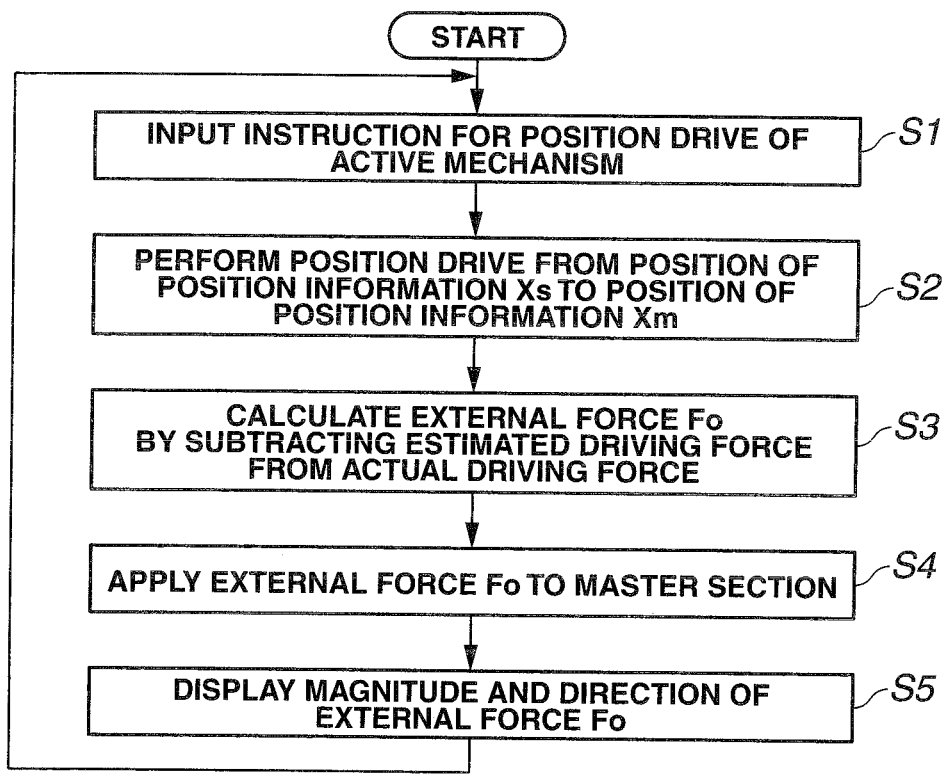
FIG. 4B is a flow chart showing a drive control procedure performed by the control system.

FIG. 4B shows a drive control procedure by the control system shown in FIG. 4A. When the operation of the control system is started, in the first step S1, an instruction input to effect the position drive (of the active mechanism 5) is performed by the operator from the master section 2 so as to change the present position information Xs of the active mechanism 5 before the instruction input to the position information Xm of the target position.

In step S2, the subtracted value (Xm–Xs) obtained from the position information Xm and Xs is inputted into the slave control section 6' including the slave driving section 6, and the slave driving section 6 performs position control (position drive) of the active mechanism 5. That is, the slave driving section 6 drives the active mechanism 5 at the position of the present position information Xs before the instruction input to the position of the target position information Xm which is instructed and inputted.

Further, the position information Xs in this case and the force Fm in the case of driving (operating) the active mechanism 5 are inputted into the force calculating section 26a (26a'). Then, as shown in step S3, the force calculating section 26a subtracts, on the basis of the above described equation (2), the estimated driving force at the time of driving the active mechanism 5 in a no-load state, from the force Fm corresponding to the actual driving force, so as to calculate the force information of the net external force Fo acting on the active mechanism 5.

The force calculating section 26a outputs the information of the force, which corresponds to the calculated external force Fo or which is proportional to the calculated external force Fo, to the master driving section 3 of the master control section 3'.

Further, as shown in step S4, the information of the external force Fo or the information of the force proportional to the external force Fo is fed back so as to be applied to the master section 2. Thereby, the operator is able to sense the net external force Fo acting on the active mechanism 5.

Further, although not shown in FIG. 4A, as shown in step S5, the force calculating section 26a displays (presents) the magnitude and direction of the external force Fo in the display section 28. After the processing in step S5, the control system returns to the processing in step S1.

The force calculating section 26a of the CPU 26 calculates the magnitude and direction of the external force Fo, to drive the master section 2 with the external force Fo or the force proportional to the external force Fo in the direction of the external force Fo, and also performs control to display the external force Fo and the direction of the external force Fo in the display section 28.

In the case of the present embodiment, the active mechanism 5 includes a plurality of, specifically, three joints 11a to 11c, and hence the force calculating section 26a calculates the external force Fo which acts on each of the joints 11a to 11c. Then, each of the joints 11a' to 11c' corresponding to the joints 11a to 11c is driven by the calculated external force Fo or the force proportional to the external force Fo.

Note that there is shown in FIG. 4B the case where the position drive is performed by the control system. However, the position and attitude of the active mechanism 5 are changed according to the rotation of each of the joints 11a to 11c, and hence the attitude drive is also performed by the control system.

According to the present embodiment, when the active mechanism 5 is actually brought into contact with a body wall, and the like, the magnitude of the external force Fo acting on the active mechanism 5 is calculated so as to include the direction of the external force Fo, and the calculation results are presented to the operator. Also, the master section 2, which is operated by the operator, is driven by the external force Fo (or the force proportional to the external force Fo), so that the operator is able to sense the external force Fo (or the force proportional to the external force Fo) by the hand operating the master section 2. Therefore, according to the present embodiment, it is possible to improve the operability in the case where the active mechanism 5 is operated in a body cavity by the operator.

Figure 5:
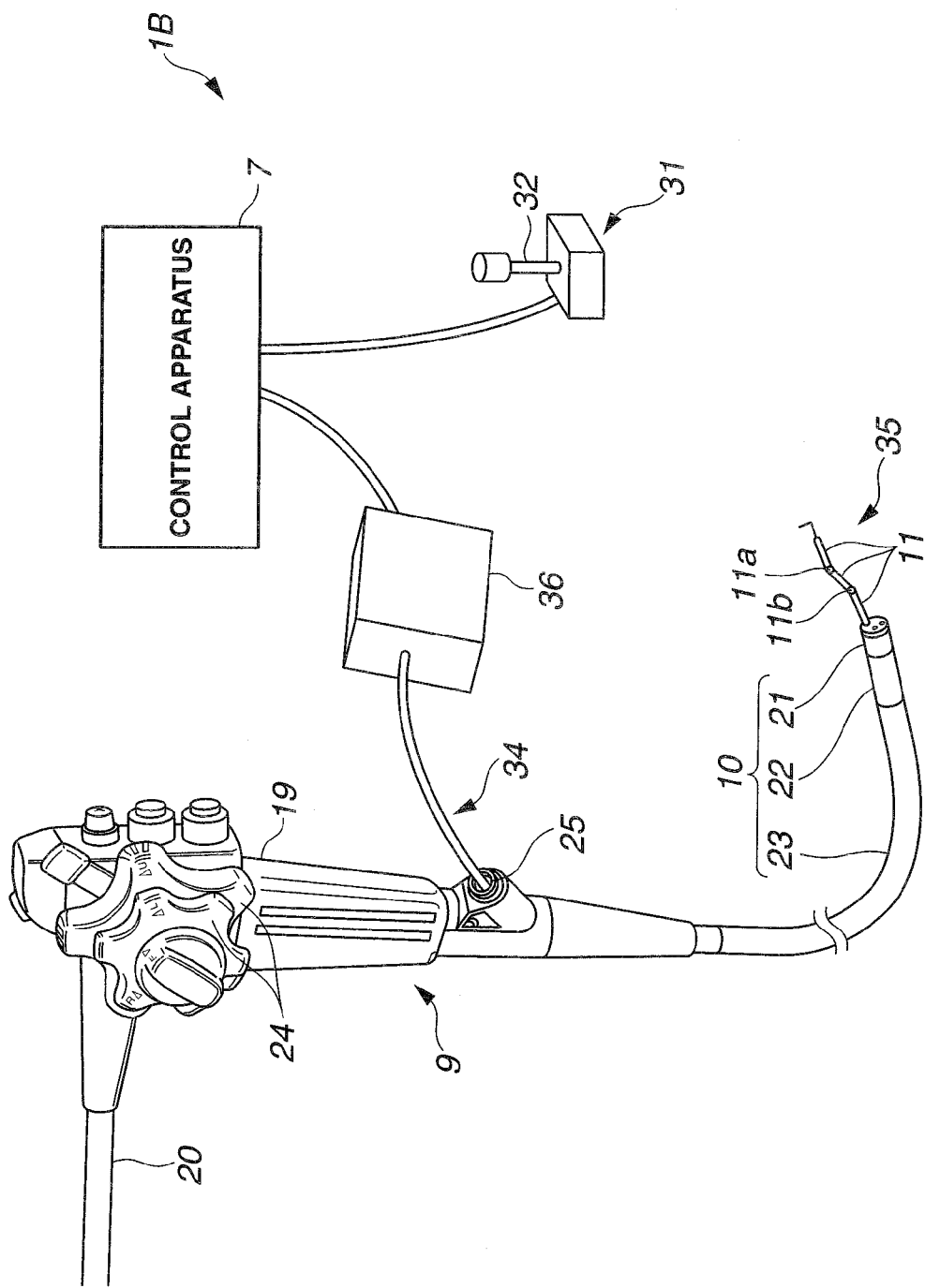
FIG. 5 is a perspective view showing an appearance of a treatment instrument system as a modification of embodiment 1.

FIG. 5 shows a configuration of a treatment instrument system 1B as a modification. In the treatment instrument system 1B, a joy stick apparatus 31 is adopted instead of the master section 2 and the master driving section 3 in the treatment instrument system 1 shown in FIG. 1.

The joy stick apparatus 31 includes a joystick 32 corresponding to the master section 2, and a driving section (not shown) which is provided on the proximal end side of the joystick 32 and by which the joystick 32 is driven to be inclined.

Further, in the treatment instrument system 1B, instead of the treatment instrument main body 4 including the openable and closable distal end cup pieces shown in FIG. 1, there is adopted a treatment instrument main body 34 including an active mechanism 35 which has, for example, an L-shaped distal end treatment section.

The active mechanism 35 has two joint shafts 11a and 11b which rotatably connect the plurality of joint pieces 11, 11 and 11. Note that the rear end of the rearmost joint piece 11 is connected to the distal end of the treatment instrument main body 34.

Figure 6:
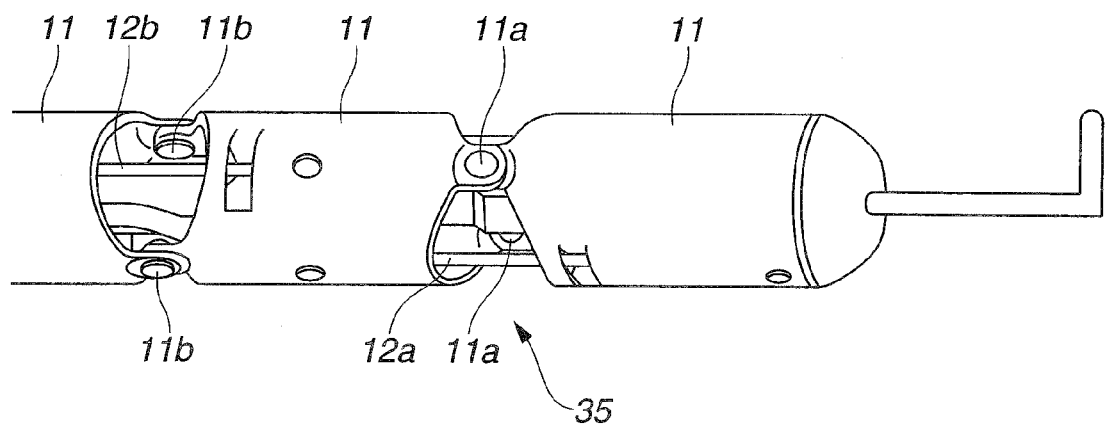
FIG. 6 is a perspective view showing a configuration of an active mechanism in the modification of embodiment 1.

FIG. 6 shows a more detailed configuration of the active mechanism 35.

The joint pieces 11, 11 and 11 are rotatably connected by the joint shafts 11a and 11b such as rivets in the directions orthogonal to each other. The wire 12a, which is inserted into the joint piece 11 and which is used to rotate the joint shaft 11a in one direction (to the substantially lower side in the paper surface in FIG. 6), is fixed in a cutout section of the joint piece 11 in front of the joint shaft 11a.

The wire 12a (not shown) which is used to rotate the joint shaft 11a in the reverse direction (to the substantially upper side in the paper surface in FIG. 6) is similarly fixed.

Further, the wire 12b which is used to rotate the joint shaft 11b in one direction (to the substantially upper side in the direction vertical to the paper surface in FIG. 6) is fixed in a cutout section of the joint piece 11 in front of the joint shaft 11b. The wire 12b (not shown) which is used to rotate the joint shaft 11b in the reverse direction is similarly fixed.

In the present modification, for example, a motor box 36, which is shown in FIG. 5 and serves as a slave driving section, is configured such that the number of the motors and encoders in the slave driving section 6 shown in FIG. 2 is reduced from three to two, respectively. Further, in the motor box 36, the number of the tension sensors shown in FIG. 2 is reduced from six to four.

The number of the motors and encoders (both not shown) on the side of the joy stick apparatus 31 is also reduced similarly to the case of the motor box 36.

Further, in the present modification, for example, the tilting (rotation) of the joystick 32 in the vertical direction is made to correspond to the rotation of the joint shaft 11a, and the tilting (rotation) in the right and left direction of the joystick 32 is made to correspond to the rotation of the joint shaft 11b.

When the operator tilts the joystick 32, for example, in the vertical direction, the CPU in the control apparatus 7 performs, on the basis of the detection signal of the encoder as a position sensor for detecting the tilting angle of the joystick 32, control via the motor driver so as to rotate the corresponding joint piece 11 in the active mechanism 35 around the joint shaft 11a'.

The other configuration of the present modification is the same as the configuration of embodiment 1. In the present modification, by the tilting operation of the joystick 32, it is possible to control the active mechanism 35 to the attitude state corresponding to the tilting operation.

Further, similarly to the case of embodiment 1, when the active mechanism 35 is brought into contact with a body wall, and the like, the external force acting on the active mechanism 35 is calculated by the force calculating section in the control apparatus 7, so as to be displayed in the display section of the control apparatus 7. Also, the force information is fed back to the joystick 32, that is, the force sense feedback is effected to the joystick 32.

Therefore, the operator operating the joystick 32 can sense the magnitude and direction of the external force Fo acting on the active mechanism 35 which is brought into contact with the body wall, and the like. Further, the operator can also know the magnitude and direction of the external force Fo by the display in the display section. Thereby, it is possible to improve the operability in the case where treatment is performed by the operator.

Embodiment 2

Next, there will be described embodiment 2 according to the present invention with reference to FIG. 7 and FIG. 8.

Figure 7:
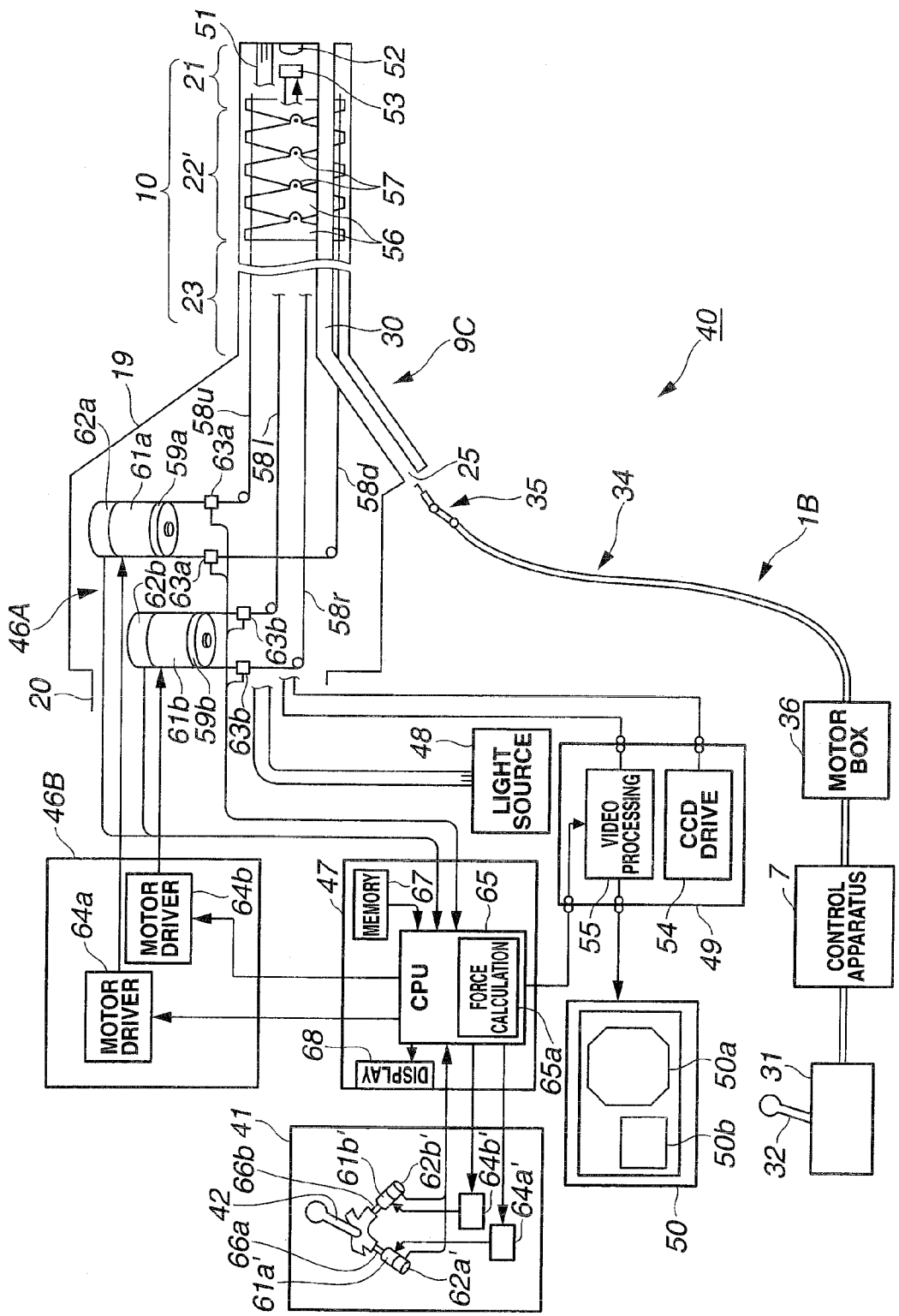
FIG. 7 is a figure showing a configuration of an endoscope system of embodiment 2 according to the present invention.

FIG. 7 shows an endoscope system 40 of embodiment 2 according to the present invention. In embodiment 1, there is adopted the endoscope 9 in which the bending section 22 is manually bent by the operator performing an operation to manually rotate the bending knob 24.

On the other hand, in the present embodiment, when the operator performs an operation (instruction input) of tilting a joystick 42 of a joy stick apparatus 41, a bending section 22', which configures an active mechanism, is electrically (actively) driven by using a driving section.

The endoscope system 40 includes an electric bending endoscope (hereinafter simply referred to as endoscope) 9C, a light source apparatus 48 which supplies illumination light to the endoscope 9C, a video processor 49 as a signal processing apparatus which performs signal processing to an image pickup device of the endoscope 9C, and a monitor 50 which displays a video signal outputted from the video processor 49.

Similarly to the endoscope 9 shown in FIG. 1, the endoscope 9C includes the insertion section 10, the operation section 19, and the universal cable 20. The insertion section 10 is configured by the distal end section 21, the bending section 22', and the flexible section 23.

Further, the treatment instrument insertion port 25 is provided near the front end of the operation section 19, and the treatment instrument insertion port 25 communicates with a channel 30 provided in the longitudinal direction of the insertion section 10. The operator can insert from the insertion port 25, for example, the treatment instrument main body 34 provided with the active mechanism 35 which forms the treatment instrument system 1B shown in FIG. 5.

Note that the operator can also perform treatment by inserting from the insertion port 25 the treatment instrument system 1 as described with reference to FIG. 1. Further, the operator can also perform treatment by inserting from the insertion port 25 a treatment tool (not shown) without the driving section.

Further, the endoscope system 40 includes the joy stick apparatus 41 having the joystick 42 which is used to perform the operation of bending instruction input, a motor box (or motor unit) 46A which serves as a driving section to drive and bend the bending section 22' in the present embodiment, and which is provided, for example, in the operation section 19, a motor drive box 46B which serves as power means (drive means) in the motor box 46A and which drives motors, and a control apparatus 47 which performs bending control of the bending section 22'.

The light source apparatus 48, to which a connector (not shown) provided at the end section of the universal cable 20 is detachably connected, generates illumination light. The illumination light is supplied to a light guide 51 of the endoscope 9C, so as to be emitted from the distal end surface of the light guide 51.

An image of a subject, such as a lesion, illuminated by the illumination light is formed at an image forming position by an objective lens 52 attached to an observation window. A charge coupled device (hereinafter abbreviated as CCD) 53 is arranged at the image forming position. The CCD 53 is connected to a CCD drive circuit 54 and a video processing circuit 55 in the video processor 49 via signal lines.

The CCD drive circuit 54 applies a CCD drive signal to the CCD 53, so as to enable the CCD 53 to output an image-pickup signal subjected to photoelectric conversion. The image pickup signal outputted from the CCD 53 is subjected to signal processing by the video processing circuit 55, so as to be converted into a video signal. Then, an optical image formed on the CCD 53 is displayed as an endoscopic image on an endoscopic image display area 50a in the display surface of the monitor 50 into which the video signal is inputted.

Further, in the bending section 22', a plurality of joint pieces or bending pieces 56 are connected to each other via rivets 57 as joint shafts (or rotary shafts) so as to be freely rotated (or bent). Note that in FIG. 7, only the rivets 57, which allows free rotation only in the direction vertical to the paper surface, are shown for simplification, but in practice, the bending pieces 56, which are adjacent to each other in the longitudinal direction, are connected by the rivets 57 so as to be freely rotated alternately in the vertical direction and the right and left direction.

Further, the distal ends of pairs of bending wires 58u and 58d; 58l and 58r, which are inserted so as to be respectively arranged in the vertical direction and the right and left direction in the insertion section 10, are fixed to the most distal end bending piece 56 or the distal end section 21. The rear ends of the pairs of bending wires are respectively fixed by being hooked onto a vertical bending pulley 59a and a left and right bending pulley 59b in the operation section 19.

Each of the pulleys 59a and 59b is rotatably connected to the rotary shaft of each of motors 61a and 61b as power means via a gear (not shown). Each of encoders 62a and 62b is connected to the rotary shaft of each of the motors 61a and 61b. The encoders 62a and 62b respectively detect the rotation angles of the motors 61a and 61b, so as to thereby detect the position and/or attitude corresponding to the bending angle of the bending piece 56 configuring the bending section 22'.

Further, tension sensors 63a and 63a; 63b and 63b, which detect the tension acting on the respective bending wires 58u and 58d; 58l and 58r, are respectively attached to the bending wires at the vicinity of the pulleys 59a and 59b. The motors 61a and 61b which drive and bend the bending section 22' are respectively connected to motor drivers 64a and 64b, so as to be rotationally driven by receiving motor drive signals from the motor drivers 64a and 64b.

Further, the motor drivers 64a and 64b are connected to a CPU 65 which configures the control apparatus 47. The CPU 65 controls the bending operation, such as the operation of the motor drivers 64a and 64b.

Further, the detection signals of the encoders 62a and 62b and the detection signals of the tension sensors 63a and 63b are also inputted into the CPU 65.

Note that in the present embodiment, there are provided the encoders 62a and 62b as position and/or attitude sensors which detect position and/or attitude information on the side of the bending section 22', and tension sensors 63a and 63b as force sensors which detect force information on the side of the bending section 22'. However, in the case where the force information can be calculated by the position and/or attitude sensors, it may be configured such that only the position and/or attitude sensors are provided.

Further, in the joystick apparatus 41, the rotary shaft of a motor 61a' as power means is connected to a roller 66a which is provided at the proximal end section of the joystick 42 and which supports the joystick 42 rotatably in the vertical direction. Further, an encoder 62a' as a position and/or attitude sensor is connected to the rotary shaft of the motor 61a', and detects the vertical tilting angle of the joystick 42 (in other words, the rotation angle of the motor 61a').

Similarly, the rotary shaft of a motor 61b' as power means is connected to a roller 66b which is provided at the proximal end section of the joystick 42 and which supports the joystick 42 rotatably in the left and right direction. Further, an encoder 62b' is connected to the rotary shaft of the motor 61b', and detects the left and right direction tilting angle of the joystick 42 (in other words, the rotation angle of the motor 61b').

Further, the motors 61a' and 61b' are connected to motor drivers 64a' and 64b', respectively. The operation of the motor drivers 64a' and 64b' is controlled by the CPU 65. The detection signals of the encoders 62a' and 62b' are inputted into the CPU 65. Then, the CPU 65 performs the bending control operation according to, for example, a program in a memory 67.

Further, the CPU 65 has a function of a force calculating section 65a configured to calculate the external force which acts at the time when the bending section 22' and the distal end section 21 on the distal end side of the bending section 22' are brought into contact with a body wall, and the like. Similarly to the case of embodiment 1, when the bending piece 56 of the bending section 22' is rotated (bent) around the rivet 57 serving as the bending shaft, the force calculating section 65a calculates the force Fo corresponding to the external force.

When the CPU 65 calculates the force Fo corresponding to the external force, then the CPU 65 performs, on the basis of the force Fo, the force control of the joystick 42 as the master section 2 (via the motor drivers 64a' and 64b').

Thereby, the operator operating the joystick 42 can sense the magnitude and direction of the external force. Note that similarly to the case of embodiment 1, the information, which is used to calculate the estimated driving force in a no-load state without the action of the external force Fo, is tabulated and stored in the memory 67. That is, the memory 67 forms a storage section of the information used for calculating the estimated driving force.

Further, the CPU 65 presents to the operator the information on the magnitude and direction of the calculated external force Fo in a display section (as a presentation section) 68 which is provided in a front panel, and the like, of the control apparatus 47, and also outputs the information to the video processing circuit 55. Then, the magnitude and direction of the external force Fo are displayed in a force information display area 50b of the display monitor 50.

Figure 8:
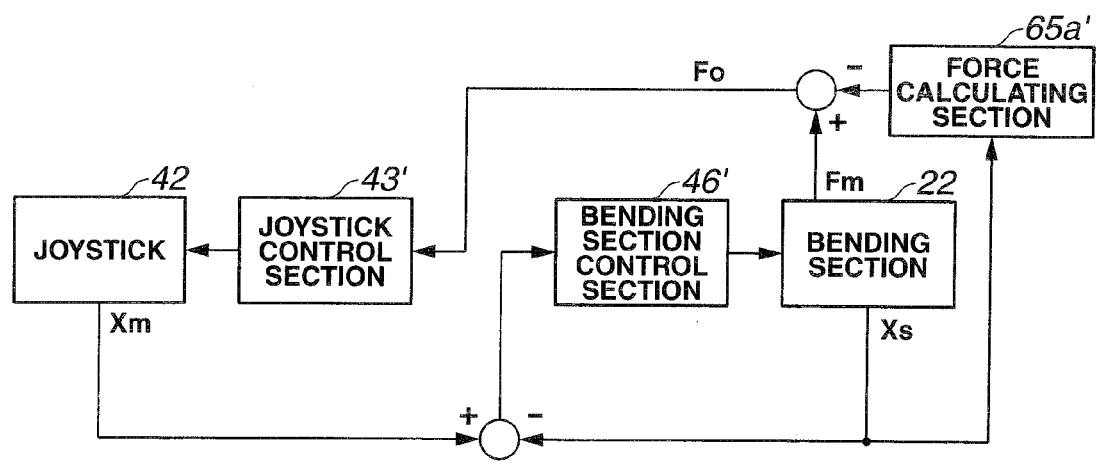
FIG. 8 is a block diagram showing a configuration of a control system of embodiment 2.

The bending control operation performed by the CPU 65 of the control apparatus 47 is configured by adopting, for example, the control system as shown in FIG. 8, which control system is basically the same as the control system shown in FIG. 4A.

That is, the control contents shown in FIG. 8 are made to be the same as the control contents shown in FIG. 4A in such a way that the master section 2 in FIG. 4A is replaced by the joystick 42, that the master control section 3' is similarly replaced by a joystick control section 43' as the control section including the driving section of the joystick 42, that the active mechanism 5 is also replaced by the bending section 22', that the slave control section 6' is replaced by a bending section control section 46' as the control section including the driving section of the bending section 22', and that the force calculating section 26a' is further replaced by a force calculating section 65a'.

The external force Fo calculated by the force calculating section 65a (or 65a') is given as force information to the joystick control section 43', and the joystick control section 43' drives the joystick 42 by the force corresponding to the force information.

The operation according to the present embodiment becomes an operation in the case where the active mechanism 5 in embodiment 1 is replaced by the bending section 22', or as the bending section 22' and the distal end section 21.

Also, in the present embodiment, when the distal end side of the insertion section 10 inserted into a body cavity is brought into contact with a body wall, and the like, the external force Fo acting on the bending section 22' is calculated so as to be displayed, and is force-fed back to the joystick 42 operated by the operator so as to be actually sensed by the operator, and the like.

Therefore, the present embodiment also makes it possible to improve the operability at the time when the operator performs an endoscopic examination by using the endoscope 9C or performs treatment by using a treatment instrument.

Embodiment 3

Figure 9:
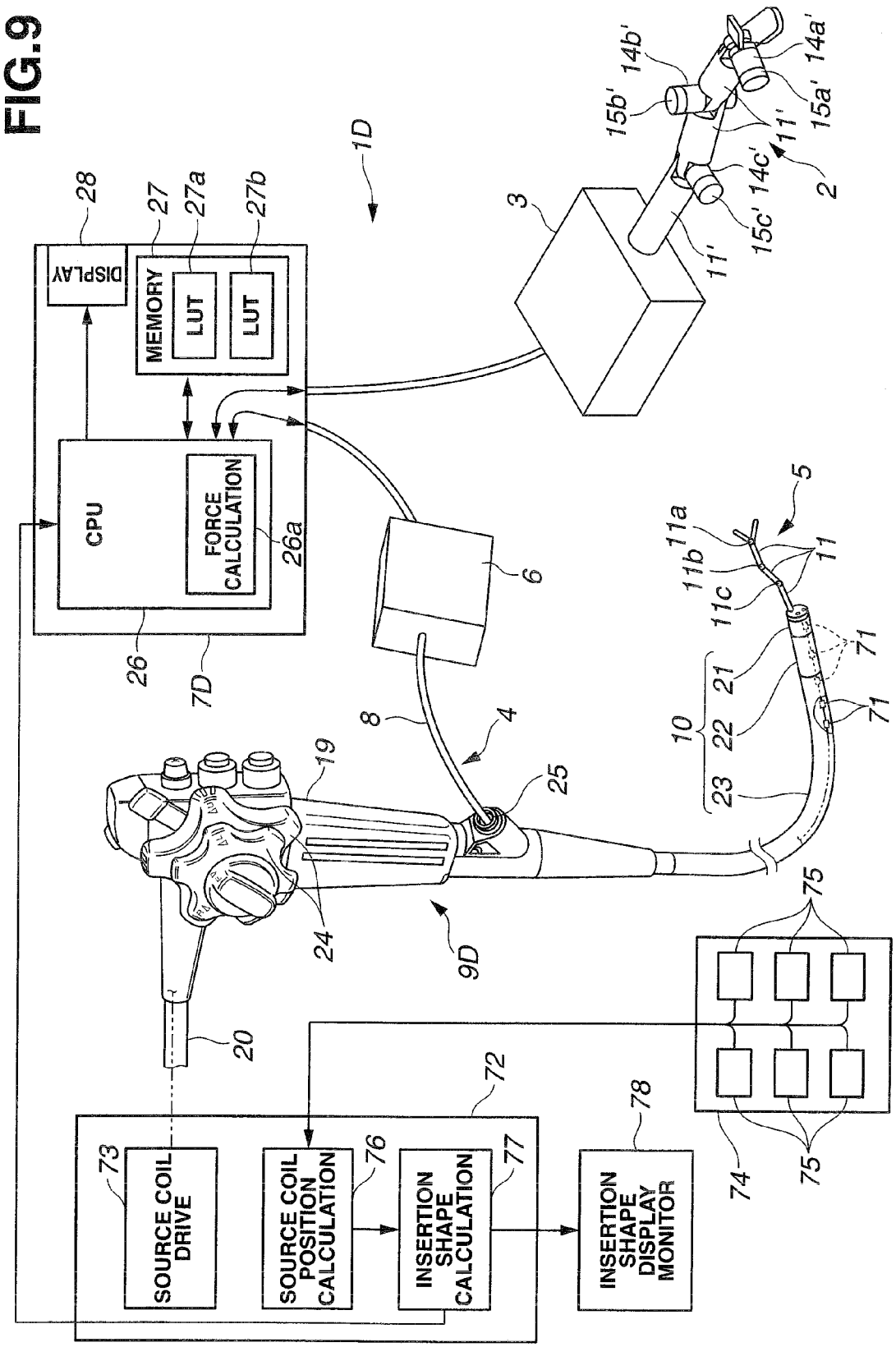
FIG. 9 is a figure showing a configuration of a treatment instrument system of embodiment 3 according to the present invention.

Next, embodiment 3 according to the present invention will be described with reference to FIG. 9 to FIG. 11. FIG. 9 shows a schematic configuration of a treatment instrument system 1D of embodiment 3 according to the present invention. The present embodiment 3 is configured such that in the treatment instrument system 1 of embodiment 1, treatment, and the like, is performed by further utilizing the attitude information (at a plurality of positions) of the insertion section 10 of an endoscope 9D.

The treatment instrument system 1D includes, in addition to the configuration shown in FIG. 1 and FIG. 2, and the like, a configuration to calculate the attitude information of the endoscope 9D.

The endoscope 9D is configured such that, in the endoscope 9 shown in FIG. 1, a plurality of coils (hereinafter referred to as source coils) 71, 71, ..., 71, which generate magnetic fields, are arranged with predetermined intervals in the longitudinal direction in the insertion section 10. The source coils 71, 71, ..., 71 are connected to a source coil drive circuit 73 in an insertion shape detecting apparatus 72 via the universal cable 20.

The source coil drive circuit 73 applies AC drive signals to the plurality of source coils 71, 71, ..., 71, so as to make a magnetic field generated around each of the source coils 71.

Further, a sense coil unit (or antenna unit) 74 is arranged around a patient (not shown) into which the insertion section 10 of the endoscope 9D is inserted. In the sense coil unit 74, there are arranged a plurality of coils (hereinafter referred to as sense coils) 75, 75, ..., 75 for detecting the magnetic fields generated by the respective source coils 71.

The detection signals detected by the plurality of sense coils 75, 75, ..., 75 are inputted into a source coil position calculating circuit 76 in the insertion shape detecting apparatus 72. The source coil position calculating circuit 76 calculates a distance from each of the sense coils 75 to each of the source coils 71 from the amplitude and phase information of the detection signals, and further calculates the position of each of the source coils 71 by using the information on (the plurality of) distances from a plurality of reference positions (positions of the sense coils 75).

The position information of the respective source coils 71 calculated by the source coil position calculating circuit 76 is inputted into an insertion shape calculating circuit 77. The insertion shape calculating circuit 77 generates a video signal of the insertion shape of the insertion section 10 by performing image processing of connecting the positions of the respective source coils 71, so as to output the generated video signal to an insertion shape display monitor 78.

Then, the calculated insertion shape of the insertion section 10 is displayed in the display screen of the insertion shape display monitor 78.

Further, the information of the insertion shape of the insertion section 10 (in other words, the attitude information of the insertion section 10), which is calculated by the insertion shape calculating circuit 77, is transmitted at a predetermined period, to the CPU 26 which configures a control apparatus 7D. The control apparatus 7D is configured by further including, in the control apparatus 7 shown in FIG. 1, a function to utilize the attitude information of the insertion section 10 of the endoscope 9D.

The information, as described in embodiment 1, on the relationship between the rotation angle and the torque in the case where the distal end cup pieces and the joint pieces 11 of the active mechanism 5 are rotated around the joint shafts is stored in the LUT 27a in the memory 27 in the control apparatus 7D.

Further, in the present embodiment, the CPU 26 corrects the torque information read from the LUT 27a on the basis of the attitude information of the insertion section 10. The correction information in this case is stored in, for example, an LUT 27b of the memory 27, so as to be related to the attitude information of the insertion section 10.

It may also be configured such that, instead of the correction based on the attitude information, there is created a table by relating the information between the rotation angle and the torque, which information is stored in the LUT 27a, also to the attitude information of the insertion section 10, and that the corresponding torque is calculated from the rotation angle and the attitude information of the insertion section 10.

Figure 10:
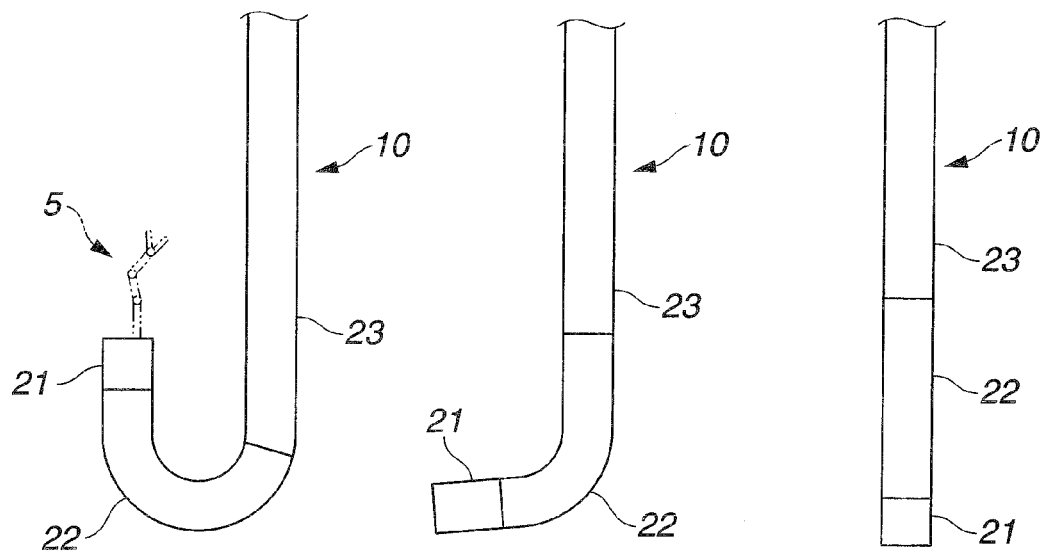
FIG. 10 is a figure showing attitude states of an insertion section of an endoscope.

The insertion shapes of the insertion section 10 as shown in FIG. 10 are inputted as the attitude information into the CPU 26 from the insertion shape calculating circuit 77.

The insertion section 10 in the state where the bending section 22 including the rear end thereof is greatly bent is shown on the leftmost side of FIG. 10. The insertion section 10 in the state where the bending section 22 is bent near the center in the longitudinal direction of the bending section 22 is shown in the middle of FIG. 10. The insertion section 10 in the state where the bending section 22 is straight is shown on the rightmost side of FIG. 10.

As shown in FIG. 10, the force Fs acting on the active mechanism 5 at the distal end of the treatment instrument main body inserted in the treatment instrument channel is changed according to the attitude of the insertion section 10. Note that, for simplification, the active mechanism 5 inserted into the treatment instrument channel is shown by two-dot chain lines only on the leftmost side of FIG. 10.

In the present embodiment, the force Fs is calculated in consideration of the attitude information of the insertion section 10. That is, the CPU 26 corrects, on the basis of the attitude information, the torque corresponding to the present rotation angle immediately before the instruction input, or calculates the torque also in consideration of the attitude information. Further, also when the CPU 26 performs the driving from the position of rotation angle or attitude which is based on the present attitude information, to the position of rotation angle or attitude which is actually instructed, the CPU 26 corrects the torque corresponding to the position of the instructed rotation angle or calculates the torque also in consideration of the attitude information.

Note that it may also be configured such that in the case where the driving is performed from the present position or attitude of the active mechanism 5 to the position or attitude instructed from the master section 2 as the instruction input section, that is, to the target position or the target attitude, and where the deviation amount between the present position and the target position or the deviation amount between the present attitude and the target attitude is small, only the torque in the present position or attitude is corrected.

Figure 11:
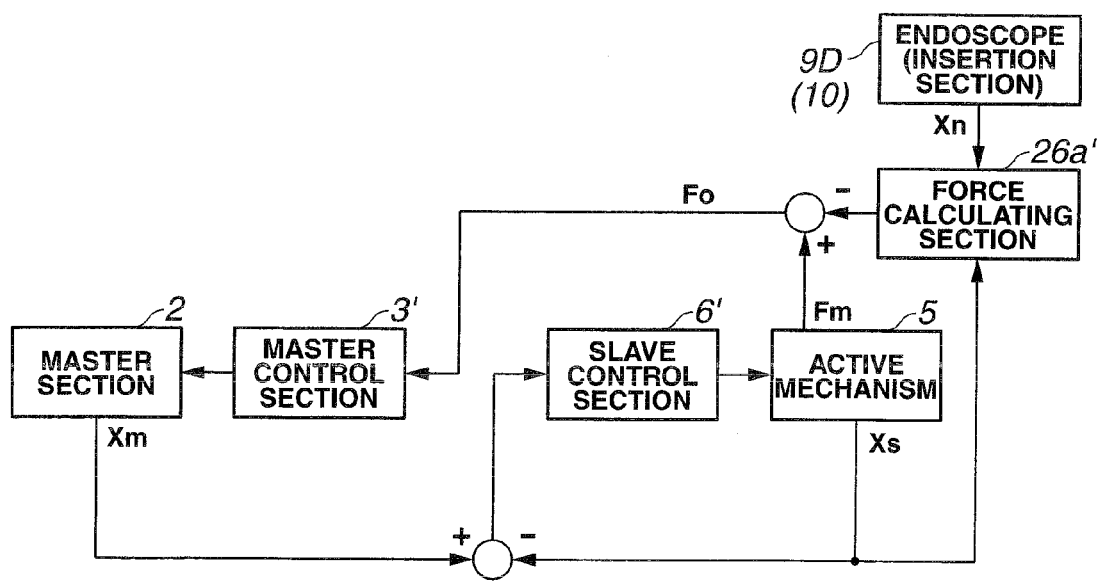
FIG. 11 is a block diagram showing a configuration of a control system of embodiment 3.

FIG. 11 shows a block diagram of the control system according to the present embodiment. The control system is configured such that in the control system shown in FIG. 4A, attitude information Xn of the insertion section 10 of the endoscope 9D is further inputted into the force calculating section 26a', and that force information F is calculated in consideration of the attitude information Xn.

The other configuration is the same as that of embodiment 1. The present embodiment has the same operation effect as that of embodiment 1. Further, the present embodiment is configured so as to calculate the external force also in consideration of the actual attitude of the insertion section 10 of the endoscope 9D, and hence is capable of calculating the external force with higher accuracy.

The other effects of the present embodiment are the same as those of embodiment 1.

Note that in the present embodiment, there are provided the position and/or attitude sensor which detect the position and/or attitude information on the side of the active mechanism 5, and the force sensor which detects the force information. However, it may also be configured such that when the force information can be calculated by the position and/or attitude sensor, only the position and/or attitude sensor is provided.

Further, the present invention can be similarly applied also in the case where, instead of the endoscope provided with the insertion section 10 having the treatment instrument channel as described above, there is used an overtube (guide tube) that has a bending section and a function of a guide member provided with a hollow channel in which a treatment instrument can be inserted, or an overtube (guide tube) in which the insertion section of the endoscope can be inserted.

Note that an embodiment configured by a method such as by partially combining the above described embodiments is also included within the scope of the present invention.

What is claimed is:

1. An active drive type medical apparatus in which a plurality of rotatable joints are provided near a distal end of a long member, the medical apparatus comprising:
   an active mechanism whose position and/or attitude is changed according to the rotation of the joints;
   an active mechanism driving section configured to electrically drive the active mechanism;
   a position/attitude detecting section provided near the rear end of the long member, and configured to detect the position and/or attitude of the active mechanism;
   an instruction input section having a plurality of rotatable joints and having a shape similar to a shape of the active mechanism, and used to perform instruction input of the position and/or attitude of the active mechanism;
   a force calculating section configured to calculate, on the basis of the instruction input of the position and/or attitude from the instruction input section, a force corresponding to a net external force acting on the active mechanism by subtracting an estimated driving force estimated in the case where the active mechanism in a no-load state is driven by the active mechanism driving section from the position and/or attitude of the active mechanism before the instruction input to the position and/or attitude instructed and inputted by the instruction input section, from a driving force required in the case where the active mechanism is actually driven by the active mechanism driving section from the position and/or attitude of the active mechanism before the instruction input to the position and/or attitude instructed and inputted by the instruction input section;
   an instruction input section driving section to which information of the force calculated by the force calculating section is inputted and which drives the plurality of joints of the instruction input section with a force proportional to the calculated force;
   a treatment instrument which includes the active mechanism;
   a guide member attitude calculating section configured to calculate an attitude in a longitudinal direction of a guide member which includes a hollow channel into which the treatment instrument is insertable and guides insertion of the treatment instrument; and
   a correcting section configured to, when the treatment instrument is inserted into the channel, correct the force in accordance with the attitude of the guide member calculated by the guide member attitude calculating section.

2. The active drive type medical apparatus according to claim 1, further comprising:
   a presentation section configured to present the information of the force calculated by the force calculating section.

3. The active drive type medical apparatus according to claim 1, further comprising:
   a presentation section configured to present the magnitude and direction of the force calculated by the force calculating section.

4. The active drive type medical apparatus according to claim 1,
   wherein the force calculating section comprises an information storage section for storing beforehand information used to calculate the estimated driving force estimated in the case where the active mechanism in a no-load state is driven by the active mechanism driving section from the position and/or attitude which is to be instructed and inputted by the instruction input section, to the position and/or attitude which is instructed and inputted by the instruction input section.

5. The active drive type medical apparatus according to claim 1,
   wherein the active mechanism comprises a bending section which is bendably formed, by using the plurality of joints rotatably joined with each other, in the axial direction of the plurality of joints.

6. The active drive type medical apparatus according to claim 1,
   wherein the active mechanism driving section is configured by a motor and a gear connected to the motor, or by a motor.

7. The active drive type medical apparatus according to claim 1,
   wherein the active drive type medical apparatus is an active treatment instrument of an electric drive system, in which the joints provided near the distal end of the long member are driven by the active mechanism driving section.

8. The active drive type medical apparatus according to claim 1,
   wherein the guide member is formed by an endoscope having a hollow channel provided therein, or by an insertion section of an overtube, and
   the force calculating section calculates the force corrected by the correcting section by using the information on the attitude of the insertion section.

9. The active drive type medical apparatus according to claim 1,
   wherein the force calculating section comprises a sensor which detects the driving force for calculating the force.

10. The active drive type medical apparatus according to claim 1, wherein the active mechanism driving section drives the joints configuring the active mechanism via wires for transmitting driving force.

11. The active drive type medical apparatus according to claim 1, further comprising a look-up table for storing correction information used to correct the force in accordance with the attitude of the guide member,
wherein the correcting section corrects the force by referring to the correction information in the look-up table.

12. The active drive type medical apparatus according to claim 11, wherein the guide member includes the hollow channel into which the treatment instrument is insertable.

13. A drive control method, comprising:
an instruction input step of operating an instruction input section and performing, to an active mechanism which includes a plurality of rotatable joints provided near a distal end of a long member and the position or attitude of which is changed according to the rotation of the joints, instruction input to change a present position/attitude to a target position/attitude, the instruction input section having a shape similar to a shape of the active mechanism and having a plurality of rotatable joints;
a driving step of driving the active mechanism from the present position/attitude to the target position/attitude;
a calculation step of calculating an external force acting on the active mechanism by subtracting an estimated driving force required to drive the active mechanism in a no-load state from the present position/attitude to the target position/attitude from a driving force required to actually drive the active mechanism from the present position/attitude to the target position/attitude;
an application step of driving the plurality of rotatable joints of the instruction input section with a force corresponding to the calculated external force and applying the force corresponding to the calculated external force to the instruction input section;
a guide member attitude calculating step of, when a treatment instrument including the active mechanism is inserted into a hollow channel provided along a longitudinal direction of a guide member which guides insertion of the treatment instrument, calculating an attitude of the guide member in the longitudinal direction; and
a correcting step of correcting the external force calculated by the calculating step, in accordance with the attitude of the guide member in the longitudinal direction calculated by the guide member attitude calculating step.

14. The drive control method according to claim 13, further comprising:
a displaying step of displaying the magnitude and direction of the external force.

15. The drive control method according to claim 13, wherein
the correcting step corrects the external force by reading, from a look-up table in which is stored correction information used to correct the external force in accordance with the attitude of the guide member, the correction information corresponding to the attitude of the guide member calculated by the guide member attitude calculating step.

* * * * *